United States Patent
Paparizos et al.

(10) Patent No.: US 6,965,046 B2
(45) Date of Patent: Nov. 15, 2005

(54) CATALYST FOR THE MANUFACTURE OF ACRYLONITRILE

(75) Inventors: Christos Paparizos, Willowick, OH (US); Michael J. Seely, Naperville, IL (US); Maria S. Friedrich, Lyndhurst, OH (US); Dev D. Suresh, Hudson, OH (US)

(73) Assignee: The Standard Oil Co., Warrenville, IL (US)

( * ) Notice: Subject to any disclaimer, the term of this patent is extended or adjusted under 35 U.S.C. 154(b) by 257 days.

(21) Appl. No.: 10/213,755

(22) Filed: Aug. 6, 2002

(65) Prior Publication Data

US 2002/0198398 A1 Dec. 26, 2002

Related U.S. Application Data

(62) Division of application No. 09/641,380, filed on Aug. 17, 2000, now Pat. No. 6,458,742.

(51) Int. Cl.$^7$ ............................................ C07C 253/24
(52) U.S. Cl. ...................... 558/319; 558/321; 558/322; 558/323; 558/324
(58) Field of Search ................................. 558/319, 322, 558/323, 321, 324; 502/215, 241, 304, 300

(56) References Cited

U.S. PATENT DOCUMENTS 5,212,137 A * 5/1993 Suresh et al. ............... 502/212
5,663,113 A * 9/1997 Midorikawa et al. ........ 502/314

FOREIGN PATENT DOCUMENTS

JP 10043595 A 2/1998
JP 10043595 * 2/1998

* cited by examiner

Primary Examiner—Johann Richter
Assistant Examiner—Ebenezer Sackey
(74) Attorney, Agent, or Firm—David P. Yusko

(57) ABSTRACT

A catalyst composition comprising a complex of catalytic oxides of iron, bismuth, molybdenum, cobalt, cerium, antimony, at least one of nickel or magnesium, and at least one of lithium, sodium, potassium, rubidium, or thallium, and characterized by the following empirical formula:

$$A_aB_bC_cFe_dBi_eCo_fCe_gSb_hMo_mO_x$$

wherein

A is at least one of Cr, P, Sn, Te, B, Ge, Zn, In, Mn, Ca, W, or mixtures thereof
B is at least one of Li, Na, K, Rb, Cs, Tl, or mixtures thereof
C is least one of Ni, Mg or mixtures thereof
a is 0 to 4.0
b is 0.01 to 1.5
c is 1.0 to 10.0
d is 0.1 to 5.0
e is 0.1 to 2.0
f is 0.1 to 10.0
g is 0.1 to 2.0
h is 0.1 to 2.0
m is 12.0 to 18.0 and
x is a number determined by the valence requirements of the other elements present.

The catalyst is useful in processes for the ammoxidation of an olefin selected from the group consisting of propylene, isobutylene or mixtures thereof, to acrylonitrile, methacrylonitrile and mixtures thereof, respectively.

8 Claims, No Drawings

CATALYST FOR THE MANUFACTURE OF ACRYLONITRILE

CROSS-REFERENCE TO RELATED APPLICATIONS

This application is a Divisional of U.S. application Ser. No. 09/641,380, filed Aug. 17, 2000 now U.S. Pat. No. 6,458,742.

BACKGROUND OF THE INVENTION

1. Field of the Invention

The present invention relates to an improved catalyst for use in the ammoxidation of an unsaturated hydrocarbon to the corresponding unsaturated nitrile. In particular, the present invention is directed to an improved process and catalyst for the ammoxidation of propylene and/or isobutylene to acrylonitrile and/or methacrylonitrile, respectively. More specifically, the invention relates to a novel and improved ammoxidation catalyst comprising a complex of catalytic oxides of iron, bismuth, molybdenum, cobalt, cerium, antimony, at least one of nickel or magnesium, and at least one of lithium, sodium, potassium, rubidium, or thallium.

2. Description of the Prior Art

There are many patents related to the production of acrylonitrile by the use of bismuth-molybdenum-iron fluidized bed catalysts. In particular, Great Britain Patent 1436475; U.S. Pat. Nos. 4,766,232; 4,377,534; 4,040,978; 4,168,246; 5,223,469 and 4,863,891 are each directed to bismuth-molybdenum-iron catalysts which may be promoted with the Group II elements to produce acrylonitrile. In addition, U.S. Pat. No. 4,190,608 discloses similarly promoted bismuth-molybdenum-iron catalyst for oxidation of olefins. U.S. Pat. Nos. 5,093,299 and 5,212,137 are directed to bismuth-molybdenum promoted catalysts which show high yields of acrylonitrile.

Catalysts containing oxides of iron, bismuth and molybdenum, promoted with suitable elements, as described in the aforementioned patents have long been used for the conversion of propylene at elevated temperatures in the presence of ammonia and oxygen (usually in the form of air) to manufacture acrylonitrile.

An object of the instant invention is a novel catalyst comprising a unique combination of promoters offering better performance in the catalytic ammoxidation of propylene, isobutylene or mixtures thereof, to acrylonitrile, methacrylonitrile and mixtures thereof, respectively.

SUMMARY OF THE INVENTION

The present invention is directed to an improved catalyst and process for the ammoxidation of propylene and/or isobutylene to acrylonitrile and/or methacrylonitrile, respectively. The present invention is a novel catalyst characterized by the following empirical formula:

$$A_a B_b C_c Fe_d Bi_e Co_f Ce_g Sb_h Mo_m O_x$$

wherein

A is at least one of Cr, P, Sn, Te, B, Ge, Zn, In, Mn, Ca, W, or mixtures thereof B is at least one of Li, Na, K, Rb, Cs, Tl, or mixtures thereof C is least one of Ni, Mg or mixtures thereof a is 0 to 4.0
b is 0.01 to 1.5
c is 1.0 to 10.0
d is 0.1 to 5.0
e is 0.1 to 2.0
f is 0.1 to 10.0
g is 0.1 to 2.0
h is 0.1 to 2.0
m is 12.0 to 18.0 and
x is a number determined by the valence requirements of the other elements present.

The present invention is also directed to a process for the conversion of an olefin selected from the group consisting of propylene, isobutylene or mixtures thereof, to acrylonitrile, methacrylonitrile and mixtures thereof, respectively, by reacting in the vapor phase at an elevated temperature and pressure said olefin with a molecular oxygen containing gas and ammonia in the presence of an mixed metal oxide catalyst, wherein the catalyst has the empirical formula shown above.

DETAILED DESCRIPTION OF THE INVENTION

The present invention is directed to an ammoxidation catalyst comprising a complex of catalytic oxides of iron, bismuth, molybdenum, cobalt, cerium, antimony, at least one of nickel or magnesium, and at least one of lithium, sodium, potassium, rubidium, or thallium, characterized by the following empirical formula:

$$A_a B_b C_c Fe_d Bi_e Co_f Ce_g Sb_h Mo_m O_x$$

wherein

A is at least one of Cr, P, Sn, Te, B, Ge, Zn, In, Mn, Ca, W, or mixtures thereof B is at least one of Li, Na, K, Rb, Cs, Tl, or mixtures thereof C is least one of Ni, Mg or mixtures thereof a is 0 to 4.0
b is 0.01 to 1.5
c is 1.0 to 10.0
d is 0.1 to 5.0
e is 0.1 to 2.0
f is 0.1 to 10.0
g is 0.1 to 2.0
h is 0.1 to 2.0
m is 12.0 to 18.0 and
x is a number determined by the valence requirements of the other elements present.

The "A" component is an optional element in the above catalyst. If "A" is present, "A" is preferably selected from the group comprising Cr, P, Ge, Ca or mixtures thereof. In a preferred embodiment of the present invention, "B" is selected to be one or more of Li, Na, K, Cs, or mixtures thereof, especially preferred being Li, Cs, K or mixtures thereof. In a preferred embodiment of the present invention, "C" is a mixture of Ni and Mg, i.e. the catalyst contains both Ni and Mg.

In other preferred embodiments of the present invention, "a" may independently range from about 0.1 to 4.0, especially preferred being about 0.1 to 3.0; "b" may independently range from about 0.05 to 1.2, especially preferred being about 0.1 to 1.0; "c" may independently range from about 2.0 to 9.0, especially preferred being about 2.0 to 8.0; "d" may independently range from about 0.5 to 5.0, especially preferred being about 1.0 to 4.0; "e" may independently range from about 0.1 to 1.5, especially preferred being about 0.1 to 1.0, "f" may independently range from about 1.0 to 7.0, especially preferred being about 1.0 to 1.5; "g" may independently range from about 0.3 to 1.5, especially preferred being about 0.3 to 1.2; "h" may independently range from about 0.3 to 1.5, especially preferred being about 0.3 to 1.2; and "m" may independently range from about 13.0 to 16.0.

The catalyst of the present invention can be used either supported or unsupported. Preferably the catalyst is supported on silica, alumina zirconium, titania, or mixtures thereof, especially preferred as a catalyst support is silica. The amount of catalyst support employed may vary. Typically the support comprises between about 30 and 70 percent of total catalyst weight, more preferably about 50 percent of total catalyst weight.

Examples of catalyst compositions of this invention include:

$K_{0.2}Ni_{3.0}Mg_{2.0}Fe_{2.0}Bi_{0.5}Co_{3.5}Ce_{1.0}Sb_{0.5}Mo_{13.6}O_x$+ 50 wt % $SiO_2$ $K_{0.2}Ni_{4.5}Mg_{1.5}Fe_{2.0}Bi_{0.5}Ca_{0.2}Co_{1.7}Ce_{0.5}Sb_{0.5}Mo_{13.6}O_x$+ 50 wt % $SiO_2$ $Cs_{0.1}K_{0.1}Mg_{2.0}Fe_{2.0}Bi_{0.5}Co_{6.2}Ce_{0.5}Sb_{0.3}Mo_{13.6}O_x$+50 wt % $SiO_2$ $Cs_{0.15}Ni_{3.0}Mg_{2.5}Fe_{1.5}Bi_{0.3}Co_{3.0}Ce_{0.5}Sb_{0.5}W_{0.2}Mo_{13.0}O_x$+ 50 wt % $SiO_2$ $Cs_{0.15}Ni_{2.5}Mg_{2.5}Fe_{1.5}Bi_{0.3}Li_{1.0.2}Co_{2.8}Ce_{1.0}Sb_{0.5}Mo_{13.0}O_x$+50 wt % $SiO_2$ $Cs_{0.1}K_{0.1}Ni_{5.0}Mg_{2.5}Fe_{1.5}Bi_{0.3}P_{0.2}Co_{1.0}Ce_{0.5}Sb_{0.5}Mo_{13.0}O_x$+50 wt % $SiO_2$ $Cs_{0.1}K_{0.1}Ni_{4.0}Mg_{2.0}Fe_{2.0}Bi_{0.5}Co_{2.2}Ce_{0.3}Cr_{0.2}Sb_{0.3}Mo_{13.6}O_x$+50 wt % $SiO_2$

The catalysts of the present invention may be prepared by any of the numerous methods of catalyst preparation which are known to those of skill in the art. For example, the catalyst may be manufactured by co-precipitating the various ingredients. The co-precipitating mass may then be dried and ground to an appropriate size. Alternatively, the co-precipitated material may be slurried and spray dried in accordance with conventional techniques. The catalyst may be extruded as pellets or formed into spears in oil as is well known in the art. Alternatively, the catalyst components may be mixed with a support in the form of the slurry followed by drying or they may be impregnated on silica or other supports. For particular procedures for manufacturing the catalyst, see U.S. Pat. Nos. 5,093,299; 4,863,891 and 4,766,232 assigned to the Assignee of the present invention, herein incorporated by reference.

The "A" component of the catalyst (i.e. at least one of Cr, P, Sn, Te, B, Ge, Zn, In, Mn, Ca, W, or mixtures thereof) may be derived from any suitable source. For example, cobalt, nickel and magnesium may be introduced into the catalyst using nitrate salts. Additionally, magnesium may be introduced into the catalyst as an insoluble carbonate or hydroxide which upon heat treating results in an oxide. Phosphorus may be introduced in the catalyst as an alkaline metal salt or alkaline earth metal salt or the ammonium salt but is preferably introduced as phosphoric acid. Calcium may be added via pre-formation of calcium molybdate or by impregnation or by other means known in the art.

Typically, the "B" component of the catalyst (i.e. at least one of Li, Na, K, Rb, Cs, Tl, or mixtures thereof) may be introduced into the catalyst as an oxide or as a salt which upon calcination will yield the oxide. Preferably, salts such as nitrates which are readily available and easily soluble are used as the means of incorporating the A element into the catalyst.

Bismuth may be introduced into the catalyst as an oxide or as a salt which upon calcination will yield the oxide. The water soluble salts which are easily dispersed but form stable oxides upon heat treating are preferred. An especially preferred source for introducing bismuth is bismuth nitrate which has been dissolved in a solution of nitric acid.

To introduce the iron component into the catalyst, one may use any compound of iron which, upon calcination will result in the oxides. As with the other elements, water soluble salts are preferred for the ease with which they may be uniformly dispersed within the catalyst. Most preferred is ferric nitrate.

The molybdenum component of the catalyst may be introduced from any molybdenum oxide such as dioxide, trioxide, pentoxide or heptaoxide. However, it is preferred that a hydrolizable or decomposable molybdenum salt be utilized as the source of the molybdenum. The most preferred starting material is ammonium heptamolybdate.

The catalysts are prepared by mixing an aqueous solution of ammonium heptamolybdate with a silica sol to which a slurry containing the compounds, preferably nitrates of the other elements, is added. The solid material is then dried, denitrified and calcined. Preferably the catalyst is spray-dried at a temperature of between 110° C. to 350° C., preferably 110° C. to 250° C., most preferably 110° C. to 180° C. The denitrification temperature may range from 100° C. to 500° C., preferably 250° C. to 450° C. Finally, calcination takes place at a temperature of between 300° C. to 700° C., preferably between 350° C. to 650° C.

The catalysts of the instant invention are useful in ammoxidation processes for the conversion of an olefin selected from the group consisting of propylene, isobutylene or mixtures thereof, to acrylonitrile, methacrylonitrile and mixtures thereof, respectively, by reacting in the vapor phase at an elevated temperature and pressure said olefin with a molecular oxygen containing gas and ammonia in the presence of the catalyst.

Preferably, the ammoxidation reaction is performed in a fluid bed reactor although other types of reactors such as transport line reactors are envisioned. Fluid bed reactors, for the manufacture of acrylonitrile are well known in the prior art. For example, the reactor design set forth in U.S. Pat. No. 3,230,246, herein incorporated by reference, is suitable.

Conditions for the ammoxidation reaction to occur are also well known in the prior art as evidenced by U.S. Pat. Nos. 5,093,299; 4,863,891; 4,767,878 and 4,503,001; herein incorporated by reference. Typically, the ammoxidation process is performed by contacting propylene or isobutylene in the presence of ammonia and oxygen with a fluid bed catalyst at an elevated temperature to produce the acrylonitrile or methacrylonitrile. Any source of oxygen may be employed. For economic reasons, however, it is preferred to use air. The typical molar ratio of the oxygen to olefin in the feed should range from 0.5:1 to 4:1, preferably from 1:1 to 3:1. The molar ratio of ammonia to olefin in the feed in the reaction may vary from between 0.5:1 to 5:1. There is really no upper limit for the ammonia-olefin ratio, but there is generally no reason to exceed a ratio of 5:1 for economic reasons. Preferred feed ratios for the catalyst of the instant invention for the production of acrylonitrile are an ammonia to propylene ratio in the range of 0.9:1 to 1.3:1, and air to propylene ratio of 8.0:1 to 12.0:1.

The reaction is carried out at a temperature of between the ranges of about 260° to 600° C., preferred ranges being 310° to 500° C., especially preferred being 350° to 480° C. The contact time, although not critical, is generally in the range of 0.1 to 50 seconds, with preference being to a contact time of 1 to 15 seconds.

The products of reaction may be recovered and purified by any of the methods known to those skilled in the art. One such method involves scrubbing the effluent gases from the reactor with cold water or an appropriate solvent to remove the products of the reaction and then purifying the reaction product by distillation.

The primary utility of the catalyst of the instant invention is for the ammoxidation of propylene to acrylonitrile. However, the instant catalyst may also be used for the oxidation of propylene to acrylic acid. Such processes are typically two stage processes, wherein propylene is converted in the presence of a catalyst to primarily acrolein in the first stage and the acrolein is converted in the presence of a catalyst to primarily acrylic acid in the second stage. The catalyst described herein is suitable for use in one or both stages.

Specific Embodiments

In order to illustrate the instant invention the following examples are provided below for illustrative purposes only.

EXAMPLE

A catalyst of the formula $K_{0.2}Ni_{3.0}Mg_{2.0}Fe_{2.0}Bi_{0.5}Co_{3.5}Ce_{1.0}Sb_{0.5}Mo_{13.6}O_x$+50 wt % $SiO_2$ was prepared as follows: 196.49 g of ammonium heptamolybdate (AHM) were dissolved in 400 ml water. 625 g of silica sol containing 40% by weight $SiO_2$ was added to the AHM solution followed by 5.96 g of $Sb_2O_3$. Finally, a mixture of melted metal nitrates was added containing: 66.12 g $Fe(NO3)_3.9H_2O$, 71.39 g $Ni(NO_3)_2.6H_2O$, 83.36 g $Co(NO_3)_2.6H_2O$, 41.96 g $Mg(NO_3)_2.6H_2O$, 19.85 g $Bi(NO_3)_3.5H_2O$, 1.66 g $KNO_3$, and 89.73 g of $Ce(NH_4)_2(NO_3)_6.6H_2O$ as a 50% solution. The resultant slurry was blended and then spray dried to give 479 g catalyst. The catalyst was heat treated 3 hours at 290° C. followed by 3 hours at 425 ° C. and finally 3 hours at 600° C. to give a finished catalyst.

Comparative Examples A through G

Using the preparation described above, several other catalyst were similarly prepared which omitted one or more of cobalt, cerium or antimony from the preparation. The composition of these catalysts are as set forth below in Table 1.

In order to identify the illustrate the performance of the claimed cobalt, cerium and antimony promoted catalysts to similar catalysts omitting one or more of these elements, all catalysts were evaluated under similar reaction conditions. A feed containing a mixture of $1C_3^=/1.2NH_3/9.5$ Air was fed over the following catalysts in an 1" diameter reactor approximately at 430° C., 10 psig and 0.09 wwh. The yield of acrylonitrile was collected and measured.

TABLE 1

| Examples | Catalyst Composition (all compositions are + 50 wt % $SiO_2$) | Total $C_3^=$ Conv. | Conv. to AN |
|---|---|---|---|
| Example | $K_{0.2}Ni_{3.0}Mg_{2.0}Fe_{2.0}Bi_{0.5}Co_{3.5}Ce_{1.0}Sb_{0.5}Mo_{13.6}O_x$ | 98.0% | 79.8% |
| Comp A | $K_{0.2}Ni_{3.0}Mg_{2.0}Fe_{2.0}Bi_{0.5}$—$Ce_{1.0}Sb_{0.5}Mo_{13.6}O_x$ | 71.7% | 56.9% |
| Comp B | $K_{0.2}Ni_{3.0}Mg_{2.0}Fe_{2.0}Bi_{0.5}Co_{3.5}$—$Sb_{0.5}Mo_{13.6}O_x$ | 80.4% | 64.1% |
| Comp C | $K_{0.2}Ni_{3.0}Mg_{2.0}Fe_{2.0}Bi_{0.5}Co_{3.5}Ce_{1.0}$—$Mo_{13.6}O_x$ | 97.1% | 76.2% |
| Comp D | $K_{0.2}Ni_{3.0}Mg_{2.0}Fe_{2.0}Bi_{0.5}Co_{3.5}$—$Mo_{13.6}O_x$ | 85.7% | 67.3% |
| Comp E | $K_{0.2}Ni_{3.0}Mg_{2.0}Fe_{2.0}Bi_{0.5}$—$Sb_{0.5}Mo_{13.6}O_x$ | 79.6% | 64.2% |
| Example | $K_{0.2}Ni_{3.0}Mg_{2.0}Fe_{2.0}Bi_{0.5}Co_{3.5}Ce_{1.0}Sb_{0.5}Mo_{13.6}O_x$ | 98.0% | 79.8% |
| Comp F | $K_{0.2}Ni_{3.0}Mg_{2.0}Fe_{2.0}Bi_{0.5}$—$Ce_{1.0}$—$Mo_{13.6}O_x$ | 85.1% | 66.8% |
| Comp G | $K_{0.2}Ni_{3.0}Mg_{2.0}Fe_{2.0}Bi_{0.5}$—$Mo_{13.6}O_x$ | 79.7% | 60.4% |

Notes:
1. "Total $C_3^=$ Conv." is the mole percent per pass conversion to of propylene to all products.
2. "Conv. to AN" is the mole percent per pass conversion to of propylene to acrylonitrile.

The catalyst composition of the instant invention is unique in that it contains three promoting elements, cobalt, cerium and antimony, not previously utilized in combination in a single ammoxidation catalyst formulation. As illustrated in Table 1, for the ammoxidation of propylene to acrylonitrile, a catalyst of the instant invention has exhibited better performance than prior art catalyst containing none, one or two of these elements. More specifically, a catalyst containing cobalt, cerium and antimony showed higher overall conversion and higher conversions to acrylonitrile when propylene was ammoxidized over such catalyst at elevated temperatures in the presence of ammonia and air.

While the present invention has been described in conjunction with the specific embodiment set forth above, it is evident that many alternatives, modifications, and variations will be apparent to those skilled in the art in light of the foregoing description. Accordingly, it is intended to embrace all such alternatives, modifications and variations as fall within the spirit and broad scope of the appended claims.

The claimed invention is:

1. A process for the conversion of an olefin selected from the group consisting of propylene, isobutylene or mixtures thereof, to acrylonitrile, methacrylonitrile and mixtures thereof, respectively, by reacting in the vapor phase at an elevated temperature and pressure said olefin with a molecular oxygen containing gas and ammonia in the presence of an oxide catalyst, wherein the catalyst has the following empirical formula:

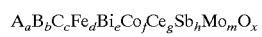

$$A_aB_bC_cFe_dBi_eCo_fCe_gSb_hMo_mO_x$$

wherein
A is at least one of Cr, P, Sn, Te, B, Ge, Zn, In, Mn, Ca, W, or mixtures thereof
B is at least one of Li, Na, K, Rb, Cs, Tl, or mixtures thereof
C is a mixture of Ni and Mg, a is 0 to 4.0,
b is 0.01 to 1.5,
c is 1.0 to 10.0,
d is 0.1 to 5.0,
e is 0.1 to 2.0,
f is 0.1 to 10.0,
g is 0.1 to 2.0,
h is 0.1 to 2.0,
m is 12.0 to 18.0 and
x is a number determined by the valence requirements of the other elements present.

2. The process of claim 1, wherein the catalyst is supported on an inert support selected from the group consisting of silica, alumina, zirconia, titania and mixtures thereof.

3. The process of claim 1, wherein B is selected from the group consisting of Na, Li, K, Cs or mixtures thereof.

4. The process of claim 1, wherein C is a mixture of Ni and Mg.

5. A process for the conversion of an olefin selected from the group consisting of propylene, isobutylene or mixtures thereof, to acrylonitrile, methacrylonitrile and mixtures thereof, respectively, comprising reacting in the vapor phase at an elevated temperature and pressure said olefin with a molecular oxygen containing gas and ammonia in the presence of an oxide catalyst, said catalyst comprising a complex of catalytic oxides of iron, bismuth, molybdenum, cobalt, cerium, antimony, at least one of nickel or magnesium, and at least one of the lithium, sodium, potassium, rubidium or thalium, wherein the relative proportions of these elements are represented by the following formula:

$A_a B_b C_c Fe_d Bi_e Co_f Ce_g Sb_h Mo_m O_x$ wherein

A is at least one of Cr, P, Sn, Te, B, Ge, Zn, In, Mn, Ca, W, or mixtures thereof B is at least one of Li, Na, K, Rb, Cs, Tl, or mixtures thereof, C is at least one of Ni, Mg or mixtures thereof, a is 0 to 4.0,
b is 0.01 to 1.5,
c is 1.0 to 10.0,
d is 0.1 to 5.0,
e is 0.1 to 2.0,
f is 0.1 to 10.0,
g is 0.1 to 2.0,
h is 0.1 to 2.0,
m is 12.0 to 18.0, and
x is a number determined by the valence requirements of the other elements present.

6. The process of claim 5, wherein the catalyst is supported on an inert support selected from the group consisting of silica, alumina, zirconia, titania and mixtures thereof.

7. The process of claim 5, wherein B is selected from the group consisting of Na, Li, K, Cs or mixtures thereof.

8. The process of claim 5, wherein C is a mixture of Ni and Mg.

* * * * *